United States Patent [19]
Budolfsen et al.

[11] Patent Number: 5,866,180
[45] Date of Patent: Feb. 2, 1999

[54] METHOD FOR PRODUCTION OF AN ACIDIFIED EDIBLE GEL ON MILK BASIS

[75] Inventors: Gitte Budolfsen, Frederiksberg; Per Munk Nielsen, Hillerød, both of Denmark

[73] Assignee: Novo Nordisk A/S, Bagsvaerd, Denmark

[21] Appl. No.: 872,440

[22] Filed: Jun. 10, 1997

Related U.S. Application Data

[63] Continuation of Ser. No. 436,405, filed as PCT/DK94/00109 Mar. 18, 1994, abandoned.

[30] Foreign Application Priority Data

Mar. 19, 1993 [DK] Denmark .................................. 0312/93

[51] Int. Cl.$^6$ ...................................................... A23C 9/12
[52] U.S. Cl. ................................ 426/42; 426/34; 426/40; 426/520; 426/522; 426/573; 426/580; 426/582; 426/583
[58] Field of Search .............................. 426/42, 34, 573, 426/580, 582, 583, 40, 520, 521, 522

[56] References Cited

U.S. PATENT DOCUMENTS 4,917,904  4/1990  Wakameda et al. ......................... 426/7
5,156,956  10/1992  Motoki et al. ........................... 426/573

OTHER PUBLICATIONS

Matsuura et al., Patent Abstracts of Japan, Abstracting 05–260893, Dec. 1993.
Nonaka et al., Patent Abstracts of Japan, Abstracting 03–160957.
Rao, D.S., Dialog Abs. No. 1258838, Indian Dairyman, vol. 43, No. 11, pp. 514–517 (1991).
Nonaka et al., J. Food Sci., vol. 57, No. 5, pp. 1214–1241 (1992).
Ajinomoto Co. et al., Chem. Abs. No. 6095n, abstract of JP 127471 Jan. 30, 1989.
Ajinomoto K.K., Abstract of JP, A, 58–149645 (Sep. 6, 1983).
Ikura et al., Dialog Abs. No. 1422994, Comments Agri. Food Chem., vol. 2, No. 6, pp. 389–407 (1992).
Ajinomoto K.K., translation of JP 59–59151 (Apr. 4, 1984).

*Primary Examiner*—Leslie Wong
*Attorney, Agent, or Firm*—Steve T. Zelson, Esq.; Valeta Gregg, Esq.

[57] ABSTRACT

The method for production of an acidified edible gel on milk basis comprises addition of transglutaminase to milk, followed by a heat treatment. Hereby a functionally and/or organoleptically satisfactory edible gel is obtained, which can be used as a yoghurt mousse or cheese.

7 Claims, No Drawings

METHOD FOR PRODUCTION OF AN ACIDIFIED EDIBLE GEL ON MILK BASIS

This application is a continuation of application Ser. No. 08/436,405 filed May 23, 1995, now abandoned, which is a national application of PCT/DK94/00109 filed Mar. 18, 1994, which claims priority of Danish application Ser. No. 0312/93 filed Mar. 19, 1993.

Many efforts have been exercised in order to generate derived milk products of nutritional value and with improved functional and/or organoleptic properties, including acidified, edible gels on milk basis. A typical example of such products is desserts, especially yoghurt and curd. In order to prepare such desserts of satisfactory quality it is necessary either to add both emulsifying agents and stabilizing agents in rather large amounts or to conduct the production process as a slow fermentation.

It is the purpose of the invention to provide a method for production of an acidified edible gel on milk basis, which exhibits satisfactory functional and/or organoleptic properties differing from the prior art acidified edible gels on milk basis like yoghurt and curd, and in relation to which it is not necessary to add any emulsifying or stabilizing agents and in relation to which it is possible to conduct the production process as a rapid pH reduction, and a use of such gel.

The method according to the invention for production of an acidified edible gel on milk basis is characterized by the fact that in a first step transglutaminase is added to milk or a milk like product, that in a second step the pH of the transglutaminase containing milk or milk like product is adjusted to 4.8 to 5.8, and that in a third step the pH-adjusted, transglutaminase containing milk or milk like product is exposed to a heat treatment.

In this specification with claims the term "milk or a milk like product" is o be understood as whole milk, skim milk, cream or a milk product with a fat content from 0% to 50% originating from any animal, preferably a cow, as such or slightly modified, e.g. by addition of flavorants. Also, it is to be understood that the milk or milk like product can be produced by suspending skim milk powder and/or full fat milk powder in an aqueous medium. Furthermore it is to be understood that the protein content of the milk or milk like product, and thus also the protein content of the acidified edible gel, is of the order of magnitude 2.0 to 6.0% w/w.

Also, it goes without saying that the concentration of $Ca^{++}$ is supposed to be of such value that $Ca^{++}$ is able to activate the transglutaminase.

Transglutaminase can be added in a dosage measured in g of pure transglutaminase per g of the protein content of the milk product, or in a dosage based on the transglutaminase activity unit, indicated in P. D. Bishop et al., Biochemistry, 29, 1990, pp. 1861–1869.

Surprisingly it has been found that the gel which has a low protein content has a pleasant consistency and mouth feeling and exhibits satisfactory organoleptic properties. These organoleptic properties can be improved by addition of flavorants to the milk or milk like product. Also, it is surprising that no emulsifying or stabilizing agents need to be added in relation to the method according to the invention. The reason for this is not completely understood, but it may be assumed as a hypothesis that the transglutaminase crosslinks the proteins in the milk or milk like product, whereby a lattice or network is generated, which do not need either emulsifying or stabilizing agents due to its own inherent stability. Furthermore, it surprisingly has been found that the production of the acidified edible gel according to the invention can be carried out with a rapid pH reduction.

From Japanese unexamined patent application No. JP-A-3-160957 a gel on the basis of a transglutaminase modified milk protein is described. However, in the prior art no pH reduction is described, and also, the protein content of the milk or milk like product used as a starting material is around 10%, i.e. much higher than in relation to this invention.

In a preferred embodiment of the method according to the invention the transglutaminase is used in an amount of between 0.1 and 0.5% w/w, related to the amount of milk protein. In this manner an edible gel with satisfactory organoleptic characteristics can be obtained.

In a preferred embodiment of the method according to the invention the transglutaminase is of human, of bovine or of microbial origin. In this manner a transglutaminase with a satisfactory activity can be obtained.

In a preferred embodiment of the method according to the invention a heat treatment is carried out between the first and the second step, preferably at a temperature between 60°–100° C., and in a time range between 0.5 and 10 minutes. In this manner an edible gel with improved organoleptic characteristics can be obtained.

In a preferred embodiment of the method according to the invention the milk or milk like product is whole milk, to which a flavorant has been added, preferably orange juice. In this manner an edible gel with improved organoleptic characteristics can be obtained.

In a preferred embodiment of the method according to the invention the heat treatment is carried out at a temperature between 60° and 140° C. and a time range between 0.5 and 20 minutes, preferably at a temperature between 70° and 100° C. and at a time range between 0.5 and 10 minutes. These intervals for temperature and time are optimal for the gelation of the transglutaminase treated milk or milk like product.

Also, the invention comprises a use of the acidified edible gel on milk basis producible by means of the method according to the invention, as a yoghurt mousse, a cheese, or as a pickling liquid for meat. In regard to the use as a pickling liquid for meat it is to be noted 1) that the transglutaminase containing milk or milk like product immediately before the heat treatment is injected into the meat or mixed intimately with the meat, and that the heat treatment is performed after the injection or the intimate mixing, and 2) that any kind of meat can be used in relation to this use, e.g. ham or fish meat. In relation to the use of the gel as a pickling liquid for meat it is to be noted that a gel cannot be injected into the meat; thus, in this case the third step of the method for production of the gel will only be performed after the injection of the pH-adjusted, transglutaminase containing milk or milk like product into the meat.

The method according to the invention will be illustrated in the following example.

EXAMPLE 1

To 100 g milk (pH 6.68) is added 0.014 g of active human transglutaminase. 9.2 g of black currant juice and 11 g of orange juice is added, whereby pH of the total mixture changes to 5.20.

100 ml of the total mixture is subsequently treated in a microwave oven or 50 seconds with an effect of 520 watt, whereby an organoleptically acceptable gel is formed.

If a similar experiment without addition of transglutaminase is performed, the end product remains liquid.

EXAMPLE 2

To 100 g portions of reconstituted skim milk made with either 9%, 15% or 30% skim milk powder is added 0.014 g, 0.023 g and 0.047 g of active human transglutaminase (FXIIIa).

The portions are then incubated at 37° C. for 45 minutes.

The portions are then acidified to pH 5.0 with HCl, Citric Acid and Glucone- delta- Lactone, respectively. The portions are then heated in a microwave oven for 50 seconds with an effect of 520 watt, whereby organoleptically acceptable gels are formed.

If a similar experiment without addition of transglutaminase is performed no gel is formed.

We claim:

1. A method for production of an acidified edible gel on milk basis, comprising
   (a) adding a transglutaminase to milk or a milk like product;
   (b) incubating the transglutaminase-containing milk product at a temperature of 37° C.;
   (c) adjusting the pH of the incubated transglutaminase-containing milk or milk like product to 4.8 to 5.8; and
   (d) a single heat treatment of the pH-adjusted, transglitaminase-containing milk or milk like product of step (c), wherein the heat treatment is carried out at a temperature range between 60°–140° C. and a time range between 0.5–20 minutes, and wherein a gel is formed as a result of the heat treatment of step (d).

2. The method of claim 1, wherein the transglutaminase is used in an amount of between 0.1 and 0.5% (w/w) relative to the amount of milk protein.

3. The method of claim 1, wherein the transglutaminase is of human, bovine or microbial origin.

4. The method of claim 1, further comprising a heat treatment step of the transglutaminase-containing milk or milk like product of step (a) at a temperature range between 60°–100° C. and a time range between 0.5–10 minutes.

5. The method of claim 1, wherein the milk or milk like product is whole milk to which a flavorant has been added.

6. The method of claim 5, wherein the flavorant is orange juice.

7. The method of claim 1, wherein the heat treatment is carried out at a temperature range between 70°–100° C. for a time range between 0.5–10 minutes.

* * * * *

UNITED STATES PATENT AND TRADEMARK OFFICE
CERTIFICATE OF CORRECTION

PATENT NO. : 5,866,180

DATED : February 2, 1999

INVENTOR(S) : Budolfsen et al.

It is certified that error appears in the above-identified patent and that said Letters Patent is hereby corrected as shown below:

Col. 1, line 34, delete "o" and insert --to--.

Col. 3, line 20, Claim 1, delete "transglitaminase" and insert --transglutaminase--.

Signed and Sealed this

Fourteenth Day of September, 1999

Attest:

Q. TODD DICKINSON

*Attesting Officer*  *Acting Commissioner of Patents and Trademarks*